United States Patent [19]

Cipris et al.

[11] Patent Number: 4,792,791
[45] Date of Patent: Dec. 20, 1988

[54] LUBRICANT OIL MONITORING SYSTEM AND METHOD OF MONITORING LUBRICANT OIL QUALITY

[75] Inventors: Divna Cipris, Millburn; Thirumalai G. Palanisamy, Morristown; Arthur T. Walsh, Morris Plains, all of N.J.

[73] Assignee: Allied-Signal Inc., Morris Township, Morris County, N.J.

[21] Appl. No.: 67,983

[22] Filed: Jun. 30, 1987

[51] Int. Cl.[4] ............................................. G08B 21/00
[52] U.S. Cl. ...................................... 340/603; 340/59
[58] Field of Search ..................... 340/603, 631, 59; 73/61.1 R, 53, 64

[56] References Cited

U.S. PATENT DOCUMENTS 4,675,662  6/1987  Kondo et al. .................. 340/59 X Primary Examiner—Stewart J. Levy
Assistant Examiner—Joseph W. Roskos
Attorney, Agent, or Firm—Anibal Jose Cortina; Gerhard H. Fuchs

[57] ABSTRACT

The invention relates to a sensor system for in-situ monitoring of lubricant oil quality. The sensor system consists of a sensing element located in-situ in contact with lubricant oil. The sensor is corrodable and upon deterioration of the oil the sensor corrodes and eventually the circuit will break. Current flow through the circuit is monitored by conventional power supply and measuring devices and upon breaking of the sensor, an indication is provided to the driver of a motor vehicle indicating that oil is to be changed.

9 Claims, 1 Drawing Sheet

LUBRICANT OIL MONITORING SYSTEM AND METHOD OF MONITORING LUBRICANT OIL QUALITY

CROSS-REFERENCE TO RELATED APPLICATIONS

This application is related to copending application Ser. No. 67,982 concurrently filed herewith, whose disclosure is specifically incorporated by reference herein.

BACKGROUND OF THE INVENTION

This invention relates to a sensor system for in-situ monitoring of lubricant oil quality and to a method of monitoring the lubricant oil quality in-situ. More specifically, the invention relates to a microprocessor controlled solid-state monitor of lubricant oil quality for use especially in automotive, as well as other motive applications.

Lubricant oil in use in automotive applications or other combustion engine applications is subjected to an aging process as a result of its use in the engine operation. The exposure of oil to high temperature zones in the presence of $NO_x$, moisture and air are main factors contributing to chemical changes which decrease the oils' lubricating effectiveness.

As a result of this decrease in its effectiveness, detrimental effects may result on the engine parts, for example, accelerated corrosion. As a further aspect of its use in a lubricant environment in automotive engines, corrosivity of lubricant oil increases with use due to the oil degradation as well as a break up of the protective additives therein. The extent of oil degradation and break up of protective additives depends on various factors such as base oil formulation, type and amount of protective additives, engine design and vehicle operating conditions. Accordingly, the customary change of oil at regular intervals of time or mileage does not necessarily provide adequate protection for engine parts because the mileage alone is not a sufficient indication of the oil quality. More specifically, the oil, depending on the type of use may be changed either too soon, causing an unnecessary cost in oil and labor expended, or too late, contributing to damage of engine parts.

Moreover, even though the effectiveness of lubricant oil, when sold, has to meet industry established standards, oil formulations can and do vary greatly from one oil manufacturer to another. More specifically, every oil contains a number of additives which vary greatly in both quality and quantity from one manufacturer to another. The oil origin can be paraffinic, synthetic, or a mixture of both and will also vary in accordance to the refining processes employed to manufacture the oil. With respect to additives, they typically amount to 5% to 25% of a base oil and will be made up of, for example, anti-oxidants (S, N, Se, As, Zn—containing organics, phenol derivatives, chelating agents, etc.), viscosity index improvers (linear polymers such as polyolefins and the like), detergents and dispersants, friction modifiers "anti-squawk" and "anti-chatter" agents such as fatty acid esters, alcohols and amines, anti-wear agents, anti-foam agents (liquid silicone, polyethelene glycol ethers and sulfides), corrosion inhibitors/meta passivators (N-compounds, fatty acid amides, carboxylic acid derivative), and others such as preservatives, odorants and the like.

As oil ages, degradation products of various type accumulate. Moreover, accumulation of other contaminants will occur simultaneously, including mineral acids such as sulfur, nitrogen and hydrohalic based acids, soot and water. The final result is an oil whose acidity, corrosivity and viscosity has substantially increased as it reaches the end of its useful life, which as previously indicated, can result in disastrous consequences when continued in use in an internal combustion engine.

Up to now, there has been no system or method of measuring the deterioration of oil in-situ in an automotive environment. Current practices of determining oil condiion require laboratory measurements such as titration of total base numbers, i.e., TBN, which is defined as the number of miligrams of KOH required to neutralize all acidic constituents present in one gram of a sample of oil. Change in viscosity of oil is not considered to be a practical indicator of oil conditions since it varies with temperature.

The degree of additive degradation on the other hand would be a good measure of oil condition. A problem with this is that each oil contains different additives so that different sensing devices would have to be designed for different oils. At the same time, other physical properties of oil such as fluoresence, specific gravity, color, dielectric constant, interfacial tension and the like could, in principle, be used for quality control tests. However, all of these tests must necessarily be performed in a laboratory environment.

In accordance with the invention, the problem of having to conduct oil testing in a laboratory environment is thus avoided.

SUMMARY OF THE INVENTION

In one aspect the invention is directed to a sensor system for in-situ monitoring of lubricant oil quality. The sensor system comprises a sensor including a sensor element located in-situ in contact with lubricant oil employed in a combustion motive environment for supplying an electrical signal indicative of the condition of the lubricant oil. A power supply serves to supply a current to the sensor with a measuring unit connected electrically to the sensor and to the power supply in a manner completing a circuit for measuring current flow from the sensor. An indicator is connected to the measuring unit for providing a perceptible indication, upon receipt of a sigaal from the measuring unit, when an electrical signal from the sensor exceeds predetermined parameters, whereby degradation of lubricant oil beyond acceptable levels can be determined as a result of degraded oil causing the change in current from the sensor to a level beyond the predetermined parameters. As can be appreciated from this brief description, what is being measured is the change in conductivity of the fuse element in the oil which is directly determinative of the quality of the oil.

In another more specific aspect, the sensor element is a conductive element made of corrodable conductive material such as a metallic, polymeric or composite material. Preferrably, the material is of lead or lead alloy having one of Sb, Sn or Ca alloyed therewith. Alternatively, the material can be a corroding metal or alloy such as tin, zinc or iron.

In its most preferred construction, the sensor element is a conductive filament, film or foil. The film, filament or foil is either free standing or supported by a substantially non-corroding, electrically insulating material of ceramic or plastic. In still more specific aspects, the sensor element is preferably made up of multiple filaments, films or foils, with each having different characteristics one from the other such that a respective one will break upon corrosion attack correspondingly different progressive stages of lubricant deterioration. According to this embodiment, there will be specific abrupt changes of current flow from the sensor element whereby progressive indications as advance warning can be provided to a driver of an automotive ehicle to facilitate scheduled changes of oil.

Other specific features will be detailed in the detailed discussion of the invention to follow hereafter.

In an alternative aspect of the invention, it is directed to a method of in-situ monitoring of lubricant oil quality. The method comprises supplying an electric current to a sensor element located in-situ in contact with lubricant oil in use in a combustion motive environment. Current flow from the sensor is measured, including the measuring of any change i.e., W i in current flow from the sensor. A perceptible alarm indication is provided upon current flow from the sensor changing beyond predetermined parameters which have been selected to define the degradation of lubricant oil quality beyond acceptable levels.

BRIEF DESCRIPTION OF THE DRAWING

Having briefly described the invention, the same will become better understood from the following detailed discussion, taken in conjunction with the attached drawing wherein.

DETAILED DISCUSSION OF THE INVENTION

Figure 1:
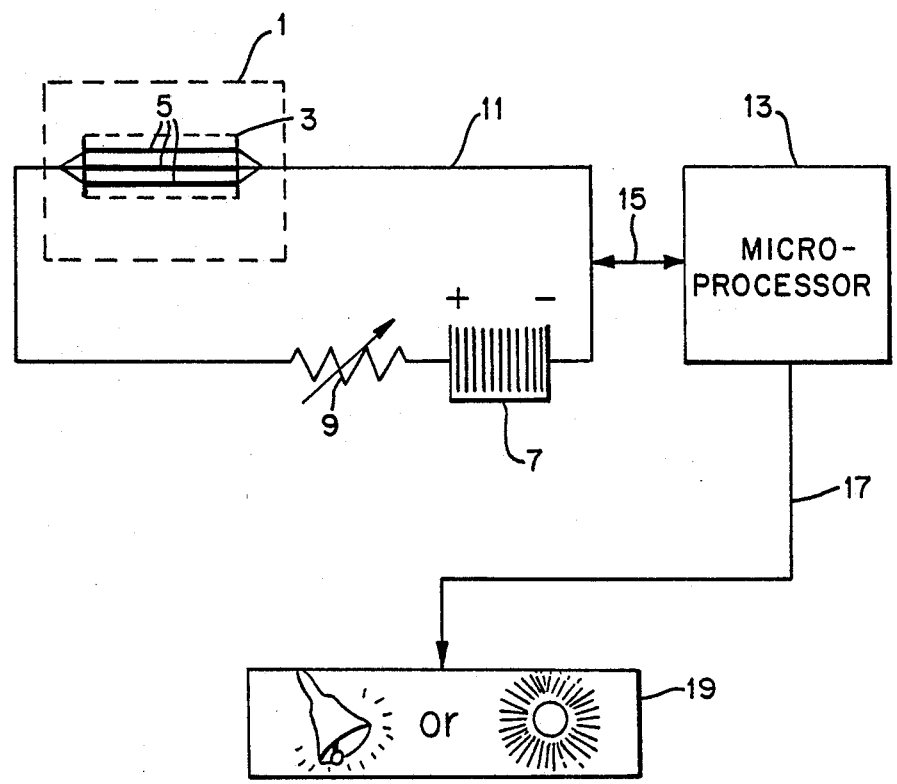
FIG. 1 is a generally schematic representation of an oil quality monitoring system and its various components.

The invention is directed to an in-situ measuring system for measuring oil corrosivity as an indicator of its condition. The rate of chemical corrosion in a given corrosive medium differs substantially from metal to metal, and their alloys or other materials. Materials which corrode sufficiently fast in lubricant oil and whose corrosion rates parallel the rate of oil degradation over a period of useful life of oil can be used as indicators of oil quality in accordance with the principles of the invention. Such materials are preferrably electrically conductive and may be metallic, polymeric or composite in nature. The corrosion rate of the selected material should be slow, for example, originally in fresh (virgin) oils, and relatively fast in spent (used) oils, gradually changing from slow to fast corrosion as the oils approach the end of their useful lives. The cumulative effects of prolonged corrosion at low (initial) rates and increased corrosion at high (later) rates are likely to be observed and are acceptable for purposes of the invention.

In an alternative embodiment, materials can be employed whose electrical and/or physical properties change significantly due to degradation or absorption of contaminants may be used in place of the above-discussed electrically conductive fuse material. For example, electrical conductivity of materials like undoped (conductive) polymers change by a large margin from a low value to a high value when they are doped. If the oil degradation products function as dopants, or swelling agents, for example, $H_2O$, then these kinds of materials are useful as an alternative construction of an oil sensor. Some composite materials have their electrical conductivity change upon absorption of contaminating/degradation products, and as a result, these types of materials may also be employed as the oil sensor in accordance with the invention. Examples of these materials include, among others, carbon filled silicone rubber. The essential features and differences between this group and the above-discussed corrodable fuse type is that while breakage occurs in the corrodable fuse type, in the latter, a significant change in selected material properties occurs which results in a change in current flow therethrough due to degradation of the oil.

The status of lubricant oils useful life is reached when the corrosion rate of any one of the above-discussed sensing elements progresses to predetermined level indicated either by a change in conductivity beyond a predetermined level, or the breaking, i.e., opening, of the specific fuse element employed. Accordingly, as will be apparent to those of ordinary skill in the art, it is important to recognize that by adjusting the physical dimensions of the sensing elements in a conventional manner, such as thickness, width, and the like, the quality of oil can be monitored along the various states along its useful life.

FIG. 1 illustrates a version of the oil sensing system in accordance with the invention. Typically, the oil sensor 1 will include an oil sensing element 3, which in one variant will include multiple filaments 5 which are corrodable and which are designed to break open at different points along the deterioration of oil quality and which can be monitored individually or collectively. Electrical lead 11 completes circuit in line with a power supply 7, i.e., typically a car battery, and the circuit is adjustable in sensitivity by means of adjusting means 9 which can be, for example, a variable resistor 9. The entire circuit is connected by line 15 to a conventional automotive microprocessor 13 of the type presently employed in automotive applications for monitoring the operation of the various systems of the automobile. Upon conductivity or current flow through sensing element 3 changing by a predetermined amount, the mirco processor will process the information and when predetermined changes are reached, will pass a signal through line 17 to an indicator panel 19 or warning alarm 19 in the cockpit of an automobile. As will be clearly evident from this preferred variant, due to the fact that multiple filaments or leads 5 are employed in the sensor, the microprocessor 13 can process the information in a manner such that progressive indications of oil corrosion or deterioration can be supplied to the panel 19 as a "lead-up" warning to enable the driver to schedule, well ahead of maximum deterioration time, service for the automobile.

As noted previously, the deterioration measuring device or sensor made of any of the above materials, can be in the form of a filament, film or foil. Alternatively, the sensing element can also be a free standing element or supported on a substrate allowing direct contact between the sensing element and oil. The substrate material may be of an inert, non-conductive material, such as ceramic, plastic, glass and the like.

The sensing element itself, i.e., the fuse is an integral part of the electrical circuit which allows the detection of continuity of the fuse, in the case where the circuit is of the type which is designed to corrode and break, by measuring the current passing through. The purpose of current flow is to allow the "reading" of the fuse condition. The break of the fuse is then indicated by an electrical open circuit condition, i.e., no current flow through the circuit. Further, the fuse is designed such that currents of very low magnitude, e.g. about $10^{-6}$ amps., are sufficient for monitoring the oil.

In its implementation, the electrical circuit does not have to be "live" on a continuous basis, and fuse condition can be periodically monitored.

As will be readily apparent to one of ordinary skill in the art, other means of monitoring the status of the sensing element may be possible and are contemplated by the broadest aspects of this invention. As an example of such an alternative method is to follow the change in conductivity of a sensing element, for example, of the type previously discussed such as the undoped conductive polymers or carbon filled silicone rubber.

In the preferred aspect where the sensing element is a corrodable element 3, its conductivity decreases due to a reduced dimension of the fuse. The magnitude of conductivity change is desirably sufficiently large to assure adequate monitoring sensitivity. This manner of monitoring is also suitable for sensing elements made of conductive polymers or other composite materials than for metallic sensors. Further, depending on the type of material used as a sensing element, an increase in conductivity may also be observed. The specific arrangement, depending upon the type of sensing fuse employed, can be implemented in a routine manner by one of ordinary skill in the art.

As discussed previously the current signal is preferably fed into a fuse monitor implemented as part of a microprocessor 13 wherein it is interpreted by the microprocessor 13 is preferred. It is also possible to monitor the continuity of the fuse, for example, by conventional analog devices such as a multimeter. With respect to the metallic type fuses where, for example, when lead is employed or a lead alloy, the alloy will have one of Sb, Sn, or Ca alloyed with the lead. Alternatively, the corrodable metallic fuse can be a pure metal or an alloy made from tin, zinc, or iron.

As a result of providing a system as described above, the precise knowledge of oil condition will contribute to a cost reduction of operating a vehicle, either through less frequent oil changes or servicing or better protection of engine and thus, extended engine life.

Having described the invention generally, the following examples are illustrative of the invention and are not intended to be limiting in any way whatsoever.

EXAMPLE 1

A fuse element made up of a coil of lead wire of 0.75 mm in diameter was immersed in an oil heated under reflux, but open to air with stirring being conducted with a magnetic bar stirrer. The oil was heated at 150°–160° C. for the duration of the experiment. Tests were conducted with virgin oil and oil after being used in a car driven for 6,000 miles. The oil was Quaker State SAE 10W-40 grade. The lead coil experienced multiple breakage after 11½ days in virgin and after 4½ days in used oil.

EXAMPLE 2

The same experiment as example 1 was conducted with a like coil of lead wire. The oil employed in this experiment was Valvoline and was used in a laboratory test engine for an equivalent of 10,000 miles. The lead coil experienced multiple breakage after 11½ days in virgin oil and after 7¾ days in used oil.

EXAMPLE 3

The same coil of example 1 was employed in a test with Sun Fleet L SAE 20W-50 oil used for varying lengths of time in a different length of laboratory test engine. The results are summarized in the following table.

TABLE 1

Corrosion Study of Lead In Lubricant Oil

| Oil Status Hrs. of Use | Fuse Breaking Point, Days |
| --- | --- |
| 0 | >30 (did not break after 30 days when experiment terminated) |
| 24 | 30 |
| 49 | 8 |
| 100 | 6 |
| 150 | 4 |
| 193 | 3 |

EXMAPLE 4

The same test as in Example 1 except that the wire was a tin wire of 0.25 mm diameters employed as the sensing element. The results were similar to Example 1.

EXAMPLE 5

The same test as in Example 1 was conducted but the fuse element was made by dipping ceramic rods into a molten lead as well as in its alloys to provide film type sensors. The results were the same as in Example 1.

EXAMPLE 6

The same test as in Example 1 was conducted with a fuse element made by mechanically attaching lead and lead alloy foil strips onto a polymeric substrate. The joint points and electrical leads were masked with epoxy type resin to prevent direct contact with oil. The results were the same as in Example 1.

What is claimed:

1. A sensor system for in-situ monitoring of lubricant oil quality comprising:

sensor means comprising a sensor element located in-situ in contact with lubricant oil employed in a combustion motive environment for supplying an electrical signal indicative of the condition of said lubricant oil, said sensor element being a conductive filament, film or foil, with said filament, film or foil being either free standing or supported by a substantially non-corroding, electrically insulating material made of ceramic or plastic, and said sensor element being constructed such that either one of multiple filaments, films or foils are provided, each having different characteristics from the other such that a respective one will break at correspondingly progressive stages of lubricant deterioration;

power supply means electrically connected to said sensor means for supplying a current thereto;

measuring means connected electrically to said sensor means and to said power supply means in a manner completing a circuit for measuring current flow from said sensor means; and indicator means connected to said measuring means for providing a perceptible indication upon receipt of a signal from said measuring means when an electrical signal from said sensor element exceeds predetermined parameters, whereby degradation of lubricant oil beyond acceptable levels can be determined as a result of degraded oil causing the change in current from said sensor means to a level beyond said predetermined parameters.

2. A sensor system as in claim 1 wherein said sensor element is a conductive element made of corrodable conductive material.

3. A senoor system as in claim 2 wherein said material is selected from the group consisting essentially of metals, polymers and composites.

4. A sensor system as in claim 3 wherein said material is selected from the group consisting essentially of lead and lead alloy having one of Sb, Sn or Ca alloyed therewith.

5. A sensor as in claim 3 wherein said material is selected from the group consisting essentially of a corroding metal and an alloy of any one of tin, zinc and iron.

6. A sensor as in claim 1 further comprising adjusting means connected to said sensor means for adjusting the sensitivity of said sensor means to a predetermined level such that said indicator means is only triggered into operation at a predetermined level of lubricant deterioration.

7. A sensor as in claim 6 wherein said adjusting means comprises a variable resistor.

8. A sensor as in claim 1 wherein said measuring means is contained in a microprocessor for controlling automotive functions of a combustion motive engine.

9. A method of in-situ monitoring of lubricant oil quality comprising:
   supplying an electric current to sensor means comprising a sensor element located in-situ in contact with lubricant oil in use in a combustion motive environment, said sensor element being a conductive filament, film or foil, with said filament, film or foil being either free standing or supported by a substantially non-corroding, electrically insulating material made of ceramic or plastic, and said sensor element being such that either one of multiple filaments, films or foils are provided, each having different characteristics from the other such that a respective one will break at correspondingly progressive stages of lubricant deterioration;
   measuring current flow from said sensor means, including measuring any change in current flow from said sensor means as a result of a break of a conductive filament film or foil of said sensor element; and
   providing a perceptible alarm indication upon current flow from said sensor means changing beyond predetermined parameters, as a result of said break, which have been selected to define a degradation of lubricant oil quality beyond acceptable levels.

* * * * *